United States Patent
Weiner et al.

(10) Patent No.: US 11,116,838 B2
(45) Date of Patent: Sep. 14, 2021

(54) CHECKPOINT INHIBITOR AND VACCINE COMBINATIONS AND USE OF SAME FOR IMMUNOTHERAPY

(71) Applicants: The Trustees of the University of Pennsylvania, Philadelphia, PA (US); INOVIO PHARMACEUTICALS, INC., Plymouth Meeting, PA (US); David Weiner, Merion, PA (US); Karuppiah Muthumani, Cherry Hill, NJ (US); Niranjan Sardesai, Blue Bell, PA (US)

(72) Inventors: David Weiner, Merion, PA (US); Karuppiah Muthumani, Cherry Hill, NJ (US); Niranjan Sardesai, Blue Bell, PA (US)

(73) Assignees: The Trustees of the University of Pennsylvania, Philadelphia, PA (US); INOVIO PHARMACEUTICALS, INC., Plymouth Meeting, PA (US)

( * ) Notice: Subject to any disclaimer, the term of this patent is extended or adjusted under 35 U.S.C. 154(b) by 488 days.

(21) Appl. No.: 15/546,740

(22) PCT Filed: Jan. 28, 2016

(86) PCT No.: PCT/US2016/015263
§ 371 (c)(1),
(2) Date: Jul. 27, 2017

(87) PCT Pub. No.: WO2016/123285
PCT Pub. Date: Aug. 4, 2016

(65) Prior Publication Data
US 2018/0015161 A1    Jan. 18, 2018

Related U.S. Application Data

(60) Provisional application No. 62/109,580, filed on Jan. 29, 2015.

(51) Int. Cl.
| A61K 39/00 | (2006.01) |
| A61K 39/395 | (2006.01) |
| C07K 16/28 | (2006.01) |
| A61K 39/12 | (2006.01) |

(52) U.S. Cl.
CPC ........ *A61K 39/395* (2013.01); *A61K 39/0011* (2013.01); *A61K 39/001153* (2018.08); *A61K 39/001156* (2018.08); *A61K 39/001157* (2018.08); *A61K 39/001186* (2018.08); *A61K 39/001188* (2018.08); *A61K 39/001189* (2018.08); *A61K 39/12* (2013.01); *A61K 39/39558* (2013.01); *C07K 16/2803* (2013.01); *C07K 16/2818* (2013.01); *C07K 16/2827* (2013.01); *A61K 2039/505* (2013.01); *A61K 2039/53* (2013.01); *A61K 2039/545* (2013.01); *A61K 2039/585* (2013.01); *C07K 2317/76* (2013.01); *C12N 2710/20034* (2013.01); *Y02A 50/30* (2018.01)

(58) Field of Classification Search
None
See application file for complete search history.

(56) References Cited

U.S. PATENT DOCUMENTS

| 9,416,165 B2 * | 8/2016 | Jones ............... G01N 33/56988 |
| 2003/0068333 A1 | 4/2003 | Mohapatra |
| 2010/0247521 A1 | 9/2010 | Jones |
| 2011/0177122 A1 | 7/2011 | Nabel |
| 2012/0219614 A1 | 8/2012 | Markham |
| 2014/0093511 A1 | 4/2014 | Lonberg |

FOREIGN PATENT DOCUMENTS

| WO | 2005097211 A2 | 10/2005 |
| WO | 2014144885 A2 | 9/2014 |
| WO | WO2014144885 | * 9/2014 |
| WO | 2015103602 | 7/2015 |

OTHER PUBLICATIONS

Almagro & Fransson, Frontiers in Bioscience 2008; 13:1619-33 (Year: 2008).*
De Genstetal., Dev Comp Immunol 2006; 30:187-98 (Year: 2006).*
Yoshinaga et al., J. Biochem 2008; 143:593-601 (Year: 2008).*
European Patent Office Communication pursuant to Article 94(3) EPC for Application No. 16744075.9, dated Jun. 18, 2019, 6 pages.
Muhammad Baghdadi et al: "Blocking monoclonal antibodies of TIM proteins as orchestrators of anti-tumor immune response", MABS, vol. 6, No. 5, Sep. 3, 2014 (Sep. 3, 2014), pp. 1124-1132, XP055452586.
Muhammad Baghdadi et al: "Combined blockade of TIM-3 and TIM-4 augments cancer vaccine efficacy against established melanomas", Cancer Immunology, Immunotherapy, vol. 62, No. 4, Nov. 10, 2012 (Nov. 10, 2012), pp. 629-637, XP055181430.

* cited by examiner

*Primary Examiner* — Meera Natarajan
(74) *Attorney, Agent, or Firm* — Riverside Law LLP

(57) ABSTRACT

Disclosed herein is a vaccine comprising an antigen and checkpoint inhibitor. Also disclosed herein is a method for enhancing an immune response in a subject. The method may comprise administering the vaccine to the subject in need thereof.

3 Claims, 6 Drawing Sheets

T Cell Response

Blockade of immune checkpoints after boost increases immune responses for anti PD-1 antibodies Blockade of immune checkpoints after boost increases immune responses- Effect of TIM3 Blockade Blockade of immune checkpoints after boost increases immune responses- Effect of LAG 3 blockade : Delivery time of blockade immune checkpoints during vaccination is critical for augmenting CD8 T cell responses (time sensitive) - Early delivery Delivery time of blockade immune checkpoints during vaccination is critical for augmenting
CD8 T cell responses (time sensitive) – Late delivery

CHECKPOINT INHIBITOR AND VACCINE COMBINATIONS AND USE OF SAME FOR IMMUNOTHERAPY

CROSS-REFERENCE TO RELATED APPLICATIONS

This application is the U.S. national stage application filed under 35 U.S.C. § 371 claiming benefit to International Patent Application No. PCT/US16/15263, filed Jan. 28, 2016, which claims priority to U.S. Provisional Application No. 62/109,580, filed Jan. 29, 2015, which are hereby incorporated by reference in their entirety.

TECHNICAL FIELD

The present invention relates to vaccines combined with checkpoint inhibitor antibodies, and use of such combination for immunotherapy.

BACKGROUND

Vaccines are used to stimulate an immune response in an individual to provide protection against and/or treatment for a particular disease. Some vaccines include an antigen to induce the immune response. Some antigens elicit a strong immune response while other antigens elicit a weak immune response. A weak immune response to an antigen can be strengthened by including an adjuvant in the vaccine. Adjuvants come in many different forms, for example, aluminum salts, oil emulsions, sterile constituents of bacteria or other pathogens, cytokines, and so forth.

Programmed cell death protein 1 also known as PD-1 is a 288 amino acid cell surface protein molecule that in humans is encoded by the PDCD1 gene. This protein is expressed in pro-B cells and is thought to play a role in their differentiation. PD1 is a type I membrane protein of 268 amino acids and a member of the extended CD28/CTLA-4 family of T cell regulators. The protein's structure includes an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals. PD-1 has two ligands, PD-L1 and PD-L2, which are members of the B7 family. PD-L1 protein is upregulated on macrophages and dendritic cells (DC) in response to LPS and GM-CSF treatment, and on T cells and B cells upon TCR and B cell receptor signaling, whereas in resting mice, PD-L1 mRNA can be detected in the heart, lung, thymus, spleen, and kidney. PD-L1 is expressed on almost all murine tumor cell lines, including PA1 myeloma, P815 mastocytoma, and B16 melanoma upon treatment with IFN-γ. PD-L2 expression is more restricted and is expressed mainly by DCs and a few tumor lines.

There are studies suggesting that PD-1 and its ligands negatively regulate immune responses. PD-1 knockout mice have been shown to develop lupus-like glomerulonephritis and dilated cardiomyopathy on the C57BL/6 and BALB/c backgrounds, respectively. In vitro, treatment of anti-CD3 stimulated T cells with PD-L1-Ig results in reduced T cell proliferation and IFN-γ secretion. It appears that upregulation of PD-L1 may allow cancers to evade the host immune system. PD-L1 expression has been shown to correlate inversely with intraepithelial CD8+ T-lymphocyte count, suggesting that PD-L1 on tumor cells may suppress antitumor CD8+ T cells.

LAG3 and TIM3 are some of the many receptor molecules on the surface of T lymphocytes that exert inhibitory functions.

T cell immunoglobulin domain and mucin domain 3 (TIM-3; also known as HAVCR2), is a human protein that is encoded by the HAVCR2 gene. TIM-3 is a protein surface receptor expressed by activated T cells of the IFNgamma-producing CD4 Th1 and CD8 cytotoxic T cells. Its ligand is galectin-9 which is abundantly expressed in the tumor microenvironment induces cell death and T cell exhaustion of CD4 and CD8 T cells. Evidence of Tim-3 as a key immune checkpoint in either tumor or viral-induced immune suppression comes from demonstration that Tim-3 expressing CD8 T cells are the most suppressed or dysfunctional population of CD8 T cell in preclinical models.

Lymphocyte activation gene 3 (Lag-3 also known as CD223) is a member of the Ig superfamily that is expressed only on activated and tolerized T cells that binds MHC-II molecules and which is known to transduce inhibitory signals. LAG-3 is markedly upregulated on exhausted T cells compared to effector or memory T cells. LAG-3 negatively regulates T cell expansion by inhibiting T cell receptor induced calcium fluxes, thus controlling the size of the T cell memory pool. Studies have shown that in the context of cancer, LAG3 is upregulated on TILs and blockade of LAG-3 can enhance antitumor T cell immune responses. Blockage of LAG-3 in a viral chronic model that evokes CD8 T cells exhaustion, can invograte the CD8 T cell responses.

Collectively, these aforementioned proteins, along with other inhibitory receptors, such as CTLA-4, are important players in the CD8 T cell exhaustion that takes place in chronic immune conditions such as chronic viral infection and cancer in both experimental models and humans. These known features and function of PD1-1, CTLA-4, TIM-3 and LAG-3 make them an appealing target for immune modulation in vaccine settings.

Vaccines are also administered in many different ways (e.g., injection, orally, etc.) into many different tissues (e.g., intramuscular, nasal, etc.). Not all delivery methods, however, are equal. Some delivery methods allow for greater compliance within a population of individuals while other delivery methods may affect immunogenicity and/or safety of the vaccine.

Accordingly, there remains a need for more effective immunotherapy using synthetic antigens combined with checkpoint inhibitors, in particular TIM-3, and LAG-3. In addition, there remains a need for improved treatment methods to improve the immune response generated from combination of checkpoint inhibitors and synthetic antigens.

SUMMARY OF THE PREFERRED EMBODIMENTS

Aspects of the present invention include compositions for enhancing an immune response against an antigen in a subject in need thereof, comprising TIM-3antibody or LAG-3 antibody in combination with a synthetic antigen capable of generating an immune response in the subject, or a biologically functional fragment or variant thereof.

The synthetic antigen can be an isolated DNA that encodes for the antigen

Preferably, the synthetic antigen can be selected from the group consisting of: hTERT, prostate, WT1, tyrosinase, NYES01, PRAME, MAGE, CMV, herpes, HIV, HPV, HCV, HBV, influenza, RSV, *Plasmodium falciparum*, and *C. difficle*.

The compositions provided herein can also include a pharmaceutically acceptable excipient.

Aspects of the invention also include methods for increasing an immune response in a subject in need thereof by administering any of the compositions provided herein to the subject. The methods of increasing an immune response can also include an electroporating step.

Further aspects of the invention include methods of administering a checkpoint inhibitor in combination with an antigen to enhance the immune response of the antigen, where the checkpoint inhibitor is delivered after a prime and boost administering of the antigen.

DETAILED DESCRIPTION OF PREFERRED EMBODIMENTS

Figure 1:
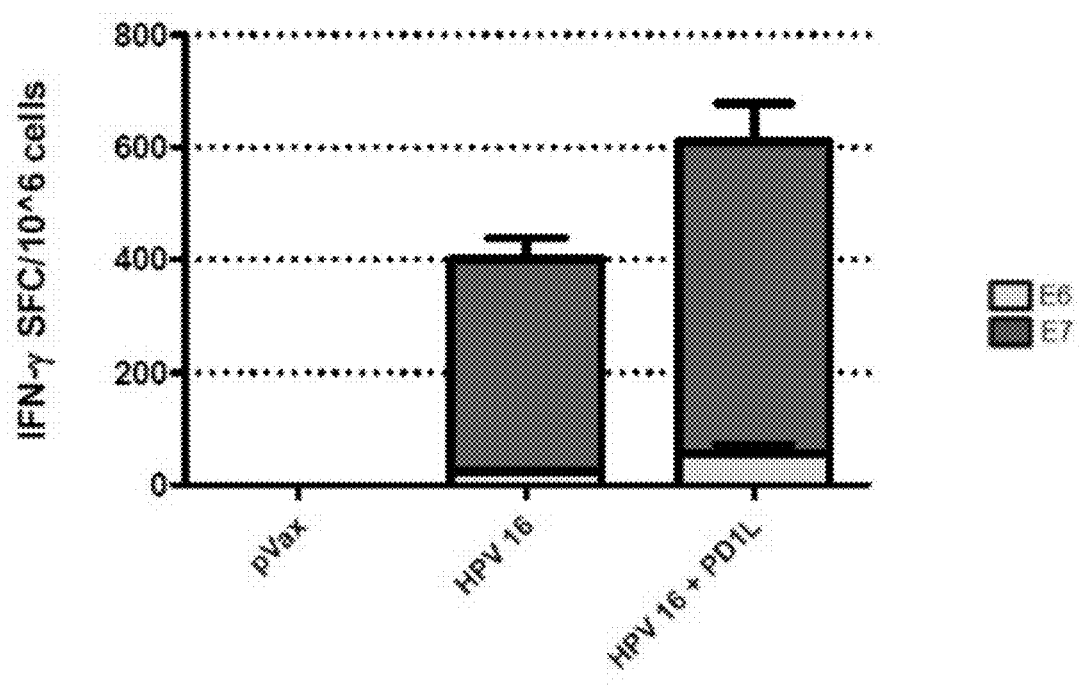
FIG. 1 provides graphs that show a 30% increase in T cell responses induced by co-therapy with anti PDL1 antibody and HPV vaccines.

The present invention relates to a vaccine that can be used to increase or enhance an immune response, ie., create a more effective immune response, by combining a vaccine, in many cases a synthetic antigen, with a checkpoint inhibitor, in particular PD1, PDL1, TIM-3, and LAG-3 antibodies. In some instances, the antibodies, in particular TIM-3 antibodies and LAG-3 antibodies, can be administered in combination with the antigen; whereas, in other instances, the antibodies, in particular TIM-3 antibodies and LAG-3 antibodies, can be administered separately from the antigen of the vaccine. In some instances the antibodies, in particular TIM-3 antibodies and LAG-3 antibodies, comprise a DNA sequence that encodes such antibody, which includes at least the variable regions of the immunoglobulin.

The vaccine of the present invention can increase the immune response to the antigen in the subject by increasing the CD8$^+$ T cell response as compared to the vaccine not including checkpoint inhibitors. This increased CD8$^+$ T cell response has cytolytic activity and secretes the anti-viral cytokine interferon-gamma (IFN-γ).

Aspects of the present invention include compositions for enhancing an immune response against an antigen in a subject in need thereof, comprising TIM-3antibody or LAG-3 antibody in combination with a synthetic antigen capable of generating an immune response in the subject, or a biologically functional fragment or variant thereof.

The synthetic antigen can be an isolated DNA that encodes for the antigen

Preferably, the synthetic antigen can be selected from the group consisting of: hTERT, prostate, WT1, tyrosinase, NYES01, PRAME, MAGE, CMV, herpes, HIV, HPV, HCV, HBV, influenza, RSV, *Plasmodium falciparum*, and *C. difficle*.

The HPV antigen can be E6 and E7 domains of subtypes selected from the group consisting of: HPV6, HPV11, HPV16, HPV18, HPV31, HPV33, HPV52, and HPV58, and a combination thereof.

The HIV antigen can be selected from the group consisting of: Env A, Env B, Env C, Env D, B Nef-Rev, and Gag, and a combination thereof.

The influenza antigen can be selected from the group consisting of: H1 HA, H2 HA, H3 HA, H5 HA, BHA antigen, and any combination thereof.

The *Plasmodium falciparum* antigen includes a circumsporozoite (CS) antigen.

The *C. difficle* antigen can be selected from the group consisting of: Toxin A, and Toxin B, and a combination thereof.

The HCV antigen can be selected from the group consisting of: E1, E2, NS3, NS4a, NS4b, NS5a, and NS5b, and a combination thereof.

The HBV antigen can be selected from the group consisting of: surface antigen type A, surface antigen type B, surface antigen type C, surface antigen type D, surface antigen type E, surface antigen type F, surface antigen type G, surface antigen type H, and core antigen, and a combination thereof.

The RSV antigen can be selected from the group consisting of: F, G, NS1, NS2, N, M, M2-1, M2-2, P, SH, and L protein, and a combination thereof.

The synthetic antigen can be hTERT, WT1 antigen, tyrosinase, NYES01, or PRAME.

The prostate antigen can be selected from the group consisting of: PSA, PSMA, STEAP, PSCA, and PAP, and a combination thereof.

The compositions provided herein can also include a pharmaceutically acceptable excipient.

Aspects of the invention also include methods for increasing an immune response in a subject in need thereof by administering any of the compositions provided herein to the subject. The methods of increasing an immune response can also include an electroporating step.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of and "consisting essentially of," the embodiments or elements presented herein, whether explicitly set forth or not.

"Adjuvant" as used herein means any molecule added to the vaccine described herein to enhance the immunogenicity of the antigens, and in particular refers to checkpoint inhibitor antibodies.

"Checkpoint inhibitor" as used herein means are inhibitors or molecules that block immune checkpoints as commonly understood in the field of cancer immunotherapy. More commonly the checkpoint inhibitors are antibodies that block these immune checkpoints, such as PD1 (on T cell) to its ligand PDL1 (on dendritic cell). Some examples of known checkpoint inhibitors include ipilimumab, pembrolizumab, nivolumab, pidilizumab, and others.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" or "immunogenic fragment" as used herein means a nucleic acid sequence or a portion thereof that encodes a polypeptide capable of eliciting an immune response in a mammal. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

Fragment or immunogenic fragment as used herein also means a polypeptide sequence or a portion thereof that is capable of eliciting an immune response in a mammal. The fragments can be polypeptide fragments selected from at least one of the various amino acid sequence set forth below. Fragments can comprise at least 10%, at least 20%, at least 30%, at least 40%, at least 50%, at least 60%, at least 70%, at least 80%, at least 90%, or at least 95% of one or more of the proteins set forth below. In some embodiments, fragments can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of at least one of the proteins set forth below.

"Genetic construct" as used herein refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a synthetic antigen, including some of the examples cited herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" as used herein can mean a mammal that wants to or is in need of being immunized with the herein described vaccine. The mammal can be a human, chimpanzee, dog, cat, horse, cow, pig, chicken mouse, or rat.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating," as used herein can mean protecting of an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Vaccine

Provided herein are vaccines comprising an antigen and checkpoint inhibitors, preferably checkpoint inhibitor antibodies. The antibodies preferably are PD1 antibody, PDL1 antibody, TIM-3antibody and/or LAG-3 antibody. The combination can be a single formulation or can be separate and administered in sequence (either antigen first and then checkpoint inhibitor, or checkpoint inhibitor first and then antigen). The vaccine can increase antigen presentation and the overall immune response to the antigen in a subject. The combination of antigen and checkpoint inhibitor induces the immune system more efficiently than a vaccine comprising the antigen alone. This more efficient immune response provides increased efficacy in the treatment and/or prevention of any disease, in particular cancer, pathogen, or virus.

The antigen and checkpoint inhibitors, preferably are PD1 antibody, PDL1 antibody, TIM-3antibody and/or LAG-3 antibody, of the vaccine can be administered together or separately to the subject in need thereof. In some instances, the checkpoint inhibitors can be administered separately from the antigen of the vaccine.

In some embodiments, the checkpoint inhibitors can be administered at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, or 96 hours before or after administration of the antigen to the subject. In other embodiments, the PD1 antibody or PDL1 antibody can be administered at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or 90 days before or after administration of the antigen to the subject.

In still other embodiments, the checkpoint inhibitors can be administered at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks before or after administration of the antigen to the subject. In other embodiments, the PD1 antibody or PDL1 antibody can be administered about 12 hours to about 15 weeks, about 12 hours to about 10 weeks, about 12 hours to about 5 weeks, about 12 hours to about 1 week, about 12 hours to about 60 hours, about 12 hours to about 48 hours, about 24 hours to about 15 weeks, about 60 hours to about 15 weeks, about 96 hours to about 15 weeks, about 1 day to about 15 weeks, about 5 days to about 15 weeks, about 10 days to about 15 weeks, about 15 days to about 15 weeks, about 20 days to about 15 weeks, about 25 days to about 15 weeks, about 30 days to about 15 weeks, about 1 week to about 15 weeks, about 5 weeks to about 15 weeks, or about 10 weeks to about 15 weeks before or after administration of the antigen to the subject.

The vaccine of the present invention can have features required of effective vaccines such as being safe so the vaccine itself does not cause illness or death; being protective against illness resulting from exposure to live pathogens such as viruses or bacteria; inducing neutralizing antibody to prevent infection of cells; inducing protective T cell against intracellular pathogens; and providing ease of administration, few side effects, biological stability, and low cost per dose. The vaccine can accomplish some or all of these features by combining the antigen with the checkpoint inhibitors, preferably the PD1 antibody, PDL1 antibody, TIM-3antibody and/or LAG-3 antibody as discussed below.

The vaccine can further modify epitope presentation within the antigen to induce greater immune response to the antigen that a vaccine comprising the antigen alone. The vaccine can further induce an immune response when administered to different tissues such as the muscle or the skin.

a. Checkpoint Inhibitors

Checkpoint inhibitors can be any antagonist to the various immune checkpoints, and are preferably antibodies that block immune checkpoints. The antibodies can be a protein including a Fab, monoclonal or polyclonal. The antibodies can also be a DNA expression construct that encodes for and can express functional antibodies. The vaccine can further comprise a TIM-3antibody or LAG-3 antibody. The antibody can be a synthetic antibody comprised of DNA sequence encoding at least the variable regions of an immunoglobulin. Such antibody can be generated by identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody. See for example methods available in Rajan, S., and Sidhu, S., *Methods in Enzymology*, vol 502, Chapter One "Simplified Synthetic Antibody Libraries (2012), which is incorporated herein in its entirety. TIM-3 and LAG-3 antibodies can also be combined with other checkpoint inhibitor antibodies, also including PD1, PDL1, CTLA4, CD40, and others. The checkpoint inhibitors can be a known product such as, for example, nivolumab, pembrolizumab, pidilizumab, BMS-936559 (See ClinicalTrials.gov Identifier NCT02028403), MPDL3280A (Roche, see ClinicalTrials.gov Identifier NCT02008227), MDX1105-01 (Bristol Myers Squibb, see ClinicalTrials.gov Identifier NCT00729664), MEDI4736 (MedImmune, See ClinicalTrials.gov Identifier NCT01693562), and MK-3475 (Merck, see ClinicalTrials.gov Identifier NCT02129556).

Synthetic Antibody (DNA Form)

The antibody can be encoded by a nucleic acid sequence (cDNA) that encodes for the elements as follows:

The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

b. Antigen

The vaccine can also comprise an antigen, or fragment or variant thereof. The antigen can be anything that induces an immune response in a subject. The antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The antigen can be contained in a protein, a nucleic acid, or a fragment thereof, or a variant thereof, or a combination thereof from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV). Preferably, the antigen can be associated with influenza or HIV.

Some antigens can induce a strong immune response. Other antigens can induce a weak immune response. The antigen can elicit a greater immune response when combined with the PD1 antibody or PDL1 antibody as described above.

(1) Viral Antigens

The antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from papilloma viruses, for example, human papillomoa virus (HPV), human immunodeficiency virus (HIV), polio virus, hepatitis viruses, for example, hepatitis A virus (HAV), hepatitis B virus (HBV), hepatitis C virus (HCV), hepatitis D virus (HDV), and hepatitis E virus (HEV), smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, or cancer causing virus.

(a) Hepatitis Antigen

The checkpoint inhibitors can be associated or combined with a hepatitis virus antigen (i.e., hepatitis antigen), or fragment thereof, or variant thereof. The hepatitis antigen can be an antigen or immunogen from hepatitis A virus (HAV), hepatitis B virus (HBV), hepatitis C virus (HCV), hepatitis D virus (HDV), and/or hepatitis E virus (HEV). In some embodiments, the hepatitis antigen can be a nucleic acid molecule(s), such as a plasmid(s), which encodes one or more of the antigens from HAV, HBV, HCV, HDV, and HEV. The hepatitis antigen can be full-length or immunogenic fragments of full-length proteins.

The hepatitis antigen can comprise consensus sequences and/or modification for improved expression. Genetic modifications including codon optimization, RNA optimization, and the addition of a high efficient immunoglobulin leader sequence to increase the immunogenicity of the constructs can be included in the modified consensus sequences. The consensus hepatitis antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codong optimized immunogens.

The hepatitis antigen can be an antigen from HAV. The hepatitis antigen can be a HAV capsid protein, a HAV non-structural protein, a fragment thereof, a variant thereof, or a combination thereof.

The hepatitis antigen can be an antigen from HCV. The hepatitis antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

The hepatitis antigen can be an antigen from HDV. The hepatitis antigen can be a HDV delta antigen, fragment thereof, or variant thereof.

The hepatitis antigen can be an antigen from HEV. The hepatitis antigen can be a HEV capsid protein, fragment thereof, or variant thereof.

The hepatitis antigen can be an antigen from HBV. The hepatitis antigen can be a HBV core protein, a HBV surface protein, a HBV DNA polymerase, a HBV protein encoded by gene X, fragment thereof, variant thereof, or combination thereof. The hepatitis antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof. The hepatitis antigen can be a consensus HBV core protein, or a consensus HBV surface protein.

In some embodiments, the hepatitis antigen can be a HBV genotype A consensus core DNA sequence construct, an IgE leader sequence linked to a consensus sequence for HBV genotype A core protein, or a HBV genotype A consensus core protein sequence.

In other embodiments, the hepatitis antigen can be a HBV genotype B consensus core DNA sequence construct, an IgE leader sequence linked to a consensus sequence for HBV genotype B core protein, or a HBV genotype B consensus core protein sequence.

In still other embodiments, the hepatitis antigen can be a HBV genotype C consensus core DNA sequence construct, an IgE leader sequence linked to a consensus sequence for HBV genotype C core protein, or a HBV genotype C consensus core protein sequence.

In some embodiments, the hepatitis antigen can be a HBV genotype D consensus core DNA sequence construct, an IgE leader sequence linked to a consensus sequence for HBV genotype D core protein, or a HBV genotype D consensus core protein sequence.

In other embodiments, the hepatitis antigen can be a HBV genotype E consensus core DNA sequence construct, an IgE leader sequence linked to a consensus sequence for HBV genotype E core protein, or a HBV genotype E consensus core protein sequence.

In some embodiments, the hepatitis antigen can be a HBV genotype F consensus core DNA sequence construct, an IgE leader sequence linked to a consensus sequence for HBV genotype F core protein, or a HBV genotype F consensus core protein sequence.

In other embodiments, the hepatitis antigen can be a HBV genotype G consensus core DNA sequence construct, an IgE leader sequence linked to a consensus sequence for HBV genotype G core protein, or a HBV genotype G consensus core protein sequence.

In some embodiments, the hepatitis antigen can be a HBV genotype H consensus core DNA sequence construct, an IgE leader sequence linked to a consensus sequence for HBV genotype H core protein, or a HBV genotype H consensus core protein sequence.

In still other embodiments, the hepatitis antigen can be a HBV genotype A consensus surface DNA sequence construct, an IgE leader sequence linked to a consensus sequence for HBV genotype A surface protein, or a HBV genotype A consensus surface protein sequence.

In some embodiments, the hepatitis antigen can be a HBV genotype B consensus surface DNA sequence construct, an IgE leader sequence linked to a consensus sequence for HBV genotype B surface protein, or a HBV genotype B consensus surface protein sequence.

In other embodiments, the hepatitis antigen can be a HBV genotype C consensus surface DNA sequence construct, an IgE leader sequence linked to a consensus sequence for HBV genotype C surface protein, or a HBV genotype C consensus surface protein sequence.

In still other embodiments, the hepatitis antigen can be a HBV genotype D consensus surface DNA sequence construct, an IgE leader sequence linked to a consensus sequence for HBV genotype D surface protein, or a HBV genotype D consensus surface protein sequence.

In some embodiments, the hepatitis antigen can be a HBV genotype E consensus surface DNA sequence construct, an IgE leader sequence linked to a consensus sequence for HBV genotype E surface protein, or a HBV genotype E consensus surface protein sequence.

In other embodiments, the hepatitis antigen can be a HBV genotype F consensus surface DNA sequence construct, an IgE leader sequence linked to a consensus sequence for HBV genotype F surface protein, or a HBV genotype F consensus surface protein sequence.

In still other embodiments, the hepatitis antigen can be a HBV genotype G consensus surface DNA sequence construct, an IgE leader sequence linked to a consensus sequence for HBV genotype G surface protein, or a HBV genotype G consensus surface protein sequence.

In other embodiments, the hepatitis antigen can be a HBV genotype H consensus surface DNA sequence construct, an IgE leader sequence linked to a consensus sequence for HBV genotype H surface protein, or a HBV genotype H consensus surface protein sequence.

(b) Human Papilloma Virus (HPV) Antigen checkpoint inhibitors can be associated or combined with a human papilloma virus (HPV) antigen, or fragment thereof, or variant thereof. The HPV antigen can be from HPV types 16, 18, 31, 33, 35, 45, 52, and 58 which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(c) RSV Antigen

The checkpoint inhibitors can also be associated or combined with an RSV antigen or fragment thereof, or variant thereof. The RSV antigen can be a human RSV fusion protein (also referred to herein as "RSV F", "RSV F protein" and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer or trimer of the RSV F protein, or a fragment or variant thereof. The RSV antigen can be an optimized amino acid RSV F amino acid sequence, or fragment or variant thereof.

The postfusion form of RSV F elicits high titer neutralizing antibodies in immunized animals and protects the animals from RSV challenge. The present invention utilizes this immunoresponse in the claimed vaccines. According to the invention, the RSV F protein can be in a prefusion form or a postfusion form.

The RSV antigen can also be human RSV attachment glycoprotein (also referred to herein as "RSV G", "RSV G protein" and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from: the RSV subtype B isolate H5601, the RSV subtype B isolate H1068, the RSV subtype B isolate H5598, the RSV subtype B isolate H1123, or a fragment or variant thereof. The RSV antigen can be an optimized amino acid RSV G amino acid sequence, or fragment or variant thereof.

In other embodiments, the RSV antigen can be human RSV non-structural protein 1 ("NS1 protein"), or fragment or variant thereof. For example, the RSV antigen can be RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein 2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have an optimized amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the optimized amino acid RSV G amino acid sequence, the human RSV genome of the RSV Long strain, the optimized amino acid RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, the RSV M2-2 protein from the RSV Long strain, the RSV L protein from the RSV Long strain, the RSV G protein from the RSV subtype B isolate H5601, the RSV G protein from the RSV subtype B isolate H1068, the RSV G protein from the RSV subtype B isolate H5598, the RSV G protein from the RSV subtype B isolate H1123, or fragment thereof, or variant thereof.

(d) Influenza Antigen

The checkpoint inhibitors can be associated or combined with an influenza antigen or fragment thereof, or variant thereof. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

In some embodiments, the influenza antigen can be H1 HA, H2 HA, H3 HA, H5 HA, or a BHA antigen. Alternatively, the influenza antigen can be a consensus hemagglutinin antigen comprising a consensus H1 amino acid sequence or a consensus H2 amino acid sequence. The consensus hemagglutinin antigen may be a synthetic hybrid consensus H1 sequence comprising portions of two different consensus H1 sequences, which are each derived from a different set of sequences from the other. An example of a consensus HA antigen that is a synthetic hybrid consensus H1 protein is a protein comprising the U2 amino acid sequence. The consensus hemagglutinin antigen may be a consensus hemagglutinin protein derived from hemagglutinin sequences from influenza B strains, such as a protein comprising the consensus BHA amino acid sequence.

The consensus hemagglutinin antigen may further comprise one or more additional amino acid sequence elements. The consensus hemagglutinin antigen may further comprise on its N-terminal an IgE or IgG leader amino acid sequence. The consensus hemagglutinin antigen may further comprise an immunogenic tag which is a unique immunogenic epitope that can be detected by readily available antibodies. An example of such an immunogenic tag is the 9 amino acid influenza HA Tag which may be linked on the consensus hemagglutinin C terminus. In some embodiments, consensus hemagglutinin antigen may further comprise on its N-terminal an IgE or IgG leader amino acid sequence and on its C terminal an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof. Examples of a consensus H1 protein include those that may consist of the consensus H1 amino acid sequence or those that further comprise additional elements such as an IgE leader sequence, or an HA Tag or both an IgE leader sequence and an HA Tag.

Examples of consensus H2 proteins include those that may consist of the consensus H2 amino acid sequence or those that further comprise an IgE leader sequence, or an HA Tag, or both an IgE leader sequence and an HA Tag.

Examples of hybrid consensus H1 proteins include those that may consist of the consensus U2 amino acid sequence or those that further comprise an IgE leader sequence, or an HA Tag, or both an IgE leader sequence and an HA Tag.

Examples of hybrid consensus influenza B hemagglutinin proteins include those that may consist of the consensus BHA amino acid sequence or it may comprise an IgE leader sequence, or an HA Tag, or both an IgE leader sequence and an HA Tag.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak's sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an H Tag at the C-terminus of the protein.

(e) Human Immunodeficiency Virus (HIV) Antigen

The checkpoint inhibitors can be associated or combined with an HIV antigen or fragment thereof, or variant thereof. HIV antigens can include modified consensus sequences for immunogens. Genetic modifications including codon optimization, RNA optimization, and the addition of a high efficient immunoglobin leader sequence to increase the immunogenicity of constructs can be included in the modified consensus sequences. The novel immunogens can be designed to elicit stronger and broader cellular immune responses than a corresponding codon optimized immunogens.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or an subtype B consensus Envelope protein sequence.

In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence.

In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments the HIV antigen can be a MPol DNA sequence or a MPol protein sequence. The HIV antigen can be nucleic acid or amino acid sequences of Env A, Env B, Env C, Env D, B Nef-Rev, Gag, or any combination thereof.

(f) Herpes Antigens Including HCMV, HSV1, HSV2, CEHV1, and VZV

The herpes antigens comprise immunogenic proteins including gB, gM, gN, gH, gL, gO, gE, gI, gK, gC, gD, UL128, UL130, UL-131A, UL-83 (pp65), whether from HCMV, HSV1, HSV2, CeHV1, or VZV. In some embodiments, the antigens can be HSV1-gH, HSV1-gL, HSV1-gC, HSV1-gD, HSV2-gH, HSV2-gL, HSV2-gC, HSV2-gD, VZV-gH, VZV-gL, VZV-gM, VZV-gN, CeHV1-gH, CeHV1-gL, CeHV1-gC, CeHV1-gD, VZV-gE, or VZV-gI.

(2) Parasite Antigens

The antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing the following diseases: Acanthamoeba keratitis, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be *Acanthamoeba, Anisakis, Ascaris lumbricoides*, Botfly, *Balantidium coli*, Bedbug, *Cestoda* (tapeworm), Chiggers, *Cochliomyia hominivorax, Entamoeba histolytica, Fasciola hepatica, Giardia lamblia*, Hookworm, *Leishmania, Linguatula serrata*, Liver fluke, Loa loa, *Paragonimus*—lung fluke, Pinworm, *Plasmodium falciparum, Schistosoma, Strongyloides stercoralis*, Mite, Tapeworm, *Toxoplasma gondii, Trypanosoma*, Whipworm, or *Wuchereria bancrofti*.

(a) Malaria Antigen

The checkpoint inhibitors can be associated or combined with a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be nucleic acid molecules such as plasmids which encode one or more of the *P. falciparum* immunogens CS; LSA1; TRAP; CelTOS; and Ama1. The immunogens may be full length or immunogenic fragments of full length proteins. The immunogens comprise consensus sequences and/or modifications for improved expression.

In other embodiments, the malaria antigen can be a consensus sequence of TRAP, which is also referred to as SSP2, designed from a compilation of all full-length *Plasmodium falciparum* TRAP/SSP2 sequences in the GenBank database (28 sequences total). Consensus TRAP immunogens (i.e., ConTRAP immunogen) may comprise a signal peptide such as an immunoglobulin signal peptide such as an IgE or IgG signal peptide and in some embodiments, may comprise an HA Tag.

In still other embodiments, the malaria antigen can be CelTOS, which is also referred to as Ag2 and is a highly conserved *Plasmodium* antigen. Consensus CelTOS antigens (i.e., ConCelTOS immunogen) may comprise a signal peptide such as an immunoglobulin signal peptide such as an IgE or IgG signal peptide and in some embodiments, may comprise an HA Tag.

In further embodiments, the malaria antigen can be Ama1, which is a highly conserved *Plasmodium* antigen. The malaria antigen can also be a consensus sequence of Ama1 (i.e., ConAma1 immunogen) comprising in some instances, a signal peptide such as an immunoglobulin signal peptide such as an IgE or IgG signal peptide and in some embodiments, may comprise an HA Tag.

In some embodiments, the malaria antigen can be a consensus CS antigen (i.e., Consensus CS immunogen) comprising in some instances, a signal peptide such as an immunoglobulin signal peptide such as an IgE or IgG signal peptide and in some embodiments, may comprise an HA Tag.

In other embodiments, the malaria antigen can be a fusion protein comprising a combination of two or more of the PF proteins set forth herein. For example, fusion proteins may comprise two or more of Consensus CS immunogen, ConLSA1 immunogen, ConTRAP immunogen, ConCelTOS immunogen and ConAma1 immunogen linked directly adjacent to each other or linked with a spacer or one or more amino acids in between. In some embodiments, the fusion protein comprises two PF immunogens; in some embodiments the fusion protein comprises three PF immunogens, in some embodiments the fusion protein comprises four PF immunogens, and in some embodiments the fusion protein comprises five PF immunogens. Fusion proteins with two Consensus PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three Consensus PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four Consensus PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1. Fusion proteins with five Consensus PF immunogens may comprise CS or CS-alt, LSA1, TRAP, CelTOS and Ama1.

In some embodiments, the fusion proteins comprise a signal peptide linked to the N terminus. In some embodiments, the fusion proteins comprise multiple signal peptides linked to the N terminal of each Consensus PF immunogen. In some embodiments, a spacer may be included between PF immunogens of a fusion protein. In some embodiments, the spacer between PF immunogens of a fusion protein may be a proteolyic cleavage site. In some embodiments, the spacer may be a proteolyic cleavage site recognized by a protease found in cells to which the vaccine is intended to be administered and/or taken up. In some embodiments, a spacer may be included between PF immunogens of a fusion protein wherein the spacer is a proteolyic cleavage site recognized by a protease found in cells to which the vaccine is intended to be administered and/or taken up and the fusion proteins comprises multiple signal peptides linked to the N terminal of each Consensus PF immunogens such that upon cleavage the signal peptide of each Consensus PF immunogens translocates the Consensus PF immunogen to outside the cell.

(3) Bacterial Antigens

The antigen can be a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, a psychrophile, an halophile, or an osmophile.

The bacterium can be an anthrax bacterium, an antibiotic resistant bacterium, a disease causing bacterium, a food poisoning bacterium, an infectious bacterium, *Salmonella bacterium, Staphylococcus bacterium, Streptococcus bacterium*, or tetanus bacterium. The bacterium can be a mycobacteria, *Clostridium tetani, Yersinia pestis, Bacillus anthraces*, methicillin-resistant *Staphylococcus aureus* (MRSA), or *Clostridium difficile*. The bacterium can be *Mycobacterium tuberculosis*.

(a) *Mycobacterium Tuberculosis* Antigens

The checkpoint inhibitors can be associated or combined with a *Mycobacterium tuberculosis* antigen (i.e., TB antigen or TB immunogen), or fragment thereof, or variant thereof.

The TB antigen can be from the Ag85 family of TB antigens, for example, Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW.

In some embodiments, the TB antigen can be nucleic acid molecules such as plasmids which encode one or more of the *Mycobacterium tuberculosis* immunogens from the Ag85 family and the Esx family. The immunogens can be full-length or immunogenic fragments of full-length proteins. The immunogens can comprise consensus sequences and/or modifications for improved expression. Consensus immunogens may comprise a signal peptide such as an immunoglobulin signal peptide such as an IgE or IgG signal peptide and in some embodiments, may comprise an HA tag.

(4) Fungal Antigens

The antigen can be a fungal antigen or fragment or variant thereof. The fungus can be *Aspergillus* species, *Blastomyces dermatitides, Candida* yeasts (e.g., *Candida albicans*), *Coccidioides, Cryptococcus neoformans, Cryptococcus gattii*, dermatophyte, *Fusarium* species, *Histoplasma capsulatum, Mucoromycotina, Pneumocystis provecii, Sporothrix schenckii, Exserohilum*, or *Cladosporium*.

(5) Cancer Markers

Markers are known proteins that are present or unregulated vis-à-vis certain cancer cells. By methodology of generating antigens that represent such markers in a way to break tolerance to self, a cancer vaccine can be generated. Such cancer vaccines can include the checkpoint inhibitors to enhance the immune response. The following are some cancer antigens:

a. hTERT hTERT is a human telomerase reverse transcriptase that synthesizes a TTAGGG tag on the end of telomeres to prevent cell death due to chromosomal shortening. Hyperproliferative cells with abnormally high expression of hTERT may be targeted by immunotherapy. Recent studies demonstrate that hTERT expression in dendritic cells transfected with hTERT genes can induce CD8+ cytotoxic T cells and elicit a CD4+ T cells in an antigen-specific fashion.

hTERT can be administered in vectors described herein, and combined with checkpoint inhibitors in various vaccination schedules, including that in the Example, below.

b. Prostate Antigens

The following are antigens capable of eliciting an immune response in a mammal against a prostate antigen. The consensus antigen can comprise epitopes that make them particularly effective as immunogens against prostate cancer cells can be induced. The consensus prostate antigen can comprise the full length translation product, a variant thereof, a fragment thereof or a combination thereof.

The prostate antigens can include one or more of the following: PSA antigen, PSMA antigen, STEAP antigen, PSCA antigen, Prostatic acid phosphatase (PAP) antigen, and other known prostate cancer markers. Proteins may comprise sequences homologous to the prostate antigens, fragments of the prostate antigens and proteins with sequences homologous to fragments of the prostate antigens.

The prostate antigens can be administered in vectors described herein, and combined with checkpoint inhibitors in various vaccination schedules, including that in the Example, below.

c. WT1

The antigen can be Wilm's tumor suppressor gene 1 (WT1), a fragment thereof, a variant thereof, or a combination thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug.

Mutation of WT1 can lead to tumor or cancer formation, for example, Wilm's tumor or tumors expressing WT1. Wilm's tumor often forms in one or both kidneys before metastasizing to other tissues, for example, but not limited to, liver tissue, urinary tract system tissue, lymph tissue, and lung tissue. Accordingly, Wilm's tumor can be considered a metastatic tumor. Wilm's tumor usually occurs in younger children (e.g., less than 5 years old) and in both sporadic and hereditary forms. Accordingly, the vaccine can be used for treating subjects suffering from Wilm's tumor. The vaccine can also be used for treating subjects with cancers or tumors that express WT1 for preventing development of such tumors in subjects. The WT1 antigen can differ from the native, "normal" WT1 gene, and thus, provide therapy or prophylaxis against an WT1 antigen-expressing tumor. Proteins may comprise sequences homologous to the WT1 antigens, fragments of the WT1 antigens and proteins with sequences homologous to fragments of the WT1 antigens.

The WT1 antigens can be administered in vectors described herein, and combined with checkpoint inhibitors in various vaccination schedules, including that in the Example, below.

d. Tyrosinase Antigen

The antigen tyrosinase (Tyr) antigen is an important target for immune mediated clearance by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-γ and TFN-α or preferably all of the aforementioned.

Tyrosinase is a copper-containing enzyme that can be found in plant and animal tissues. Tyrosinase catalyzes the production of melanin and other pigments by the oxidation of phenols such as tyrosine. In melanoma, tyrosinase can become unregulated, resulting in increased melanin synthesis. Tyrosinase is also a target of cytotoxic T cell recognition in subjects suffering from melanoma. Accordingly, tyrosinase can be an antigen associated with melanoma.

The antigen can comprise protein epitopes that make them particularly effective as immunogens against which anti-Tyr immune responses can be induced. The Tyr antigen can comprise the full length translation product, a variant thereof, a fragment thereof or a combination thereof.

The Tyr antigen can comprise a consensus protein. The Tyr antigen induces antigen-specific T-cell and high titer antibody responses both systemically against all cancer and tumor related cells. As such, a protective immune response is provided against tumor formation by vaccines comprising the Tyr consensus antigen. Accordingly, any user can design a vaccine of the present invention to include a Tyr antigen to provide broad immunity against tumor formation, metastasis of tumors, and tumor growth. Proteins may comprise sequences homologous to the Tyr antigens, fragments of the Tyr antigens and proteins with sequences homologous to fragments of the Tyr antigens.

The Tyr antigens can be administered in vectors described herein, and combined with checkpoint inhibitors in various vaccination schedules, including that in the Example, below.

e. NYES01

NY-ESO-1 is a cancer-testis antigen expressed in various cancers where it can induce both cellular and humoral immunity. Gene expression studies have shown upregulation of the gene for NY-ESO-1, CTAG1B, in myxoid and round cell liposarcomas. Proteins may comprise sequences homologous to the NYES01 antigens, fragments of the NYES01 antigens and proteins with sequences homologous to fragments of the NYES01 antigens.

The NYES01 antigens can be administered in vectors described herein, and combined with checkpoint inhibitors in various vaccination schedules, including that in the Example, below.

f. PRAME

Melanoma antigen preferentially expressed in tumors (PRAME antigen) is a protein that in humans is encoded by the PRAME gene. This gene encodes an antigen that is predominantly expressed in human melanomas and that is recognized by cytolytic T lymphocytes. It is not expressed in normal tissues, except testis. The gene is also expressed in acute leukemias. Five alternatively spliced transcript variants encoding the same protein have been observed for this gene. Proteins may comprise sequences homologous to the PRAME antigens, fragments of the PRAME antigens and proteins with sequences homologous to fragments of the PRAME antigens.

The PRAME antigens can be administered in vectors described herein, and combined with checkpoint inhibitors in various vaccination schedules, including that in the Example, below.

g. MAGE

MAGE stands for Melanoma-associated Antigen, and in particular melanoma associated antigen 4 (MAGEA4). MAGE-A4 is expressed in male germ cells and tumor cells of various histological types such as gastrointestinal, esophageal and pulmonary carcinomas. MAGE-A4 binds the oncoprotein, Gankyrin. This MAGE-A4 specific binding is mediated by its C-terminus. Studies have shown that exogenous MAGE-A4 can partly inhibit the adhesion-independent growth of Gankyrin-overexpressing cells in vitro and suppress the formation of migrated tumors from these cells in nude mice. This inhibition is dependent upon binding between MAGE-A4 and Gankyrin, suggesting that interactions between Gankyrin and MAGE-A4 inhibit Gankyrin-mediated carcinogenesis. It is likely that MAGE expression in tumor tissue is not a cause, but a result of tumor genesis, and MAGE genes take part in the immune process by targeting early tumor cells for destruction.

Melanoma-associated antigen 4 protein (MAGEA4) can be involved in embryonic development and tumor transformation and/or progression. MAGEA4 is normally expressed in testes and placenta. MAGEA4, however, can be expressed in many different types of tumors, for example, melanoma, head and neck squamous cell carcinoma, lung carcinoma, and breast carcinoma. Accordingly, MAGEA4 can be antigen associated with a variety of tumors.

The MAGEA4 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts.

The MAGEA4 antigen can comprise protein epitopes that make them particularly effective as immunogens against which anti-MAGEA4 immune responses can be induced. The MAGEA4 antigen can comprise the full length translation product, a variant thereof, a fragment thereof or a combination thereof. The MAGEA4 antigen can comprise a consensus protein.

The nucleic acid sequence encoding the consensus MAGEA4 antigen can be optimized with regards to codon usage and corresponding RNA transcripts. The nucleic acid encoding the consensus MAGEA4 antigen can be codon and RNA optimized for expression. In some embodiments, the nucleic acid sequence encoding the consensus MAGEA4 antigen can include a Kozak sequence (e.g., GCC ACC) to increase the efficiency of translation. The nucleic acid encoding the consensus MAGEA4 antigen can include multiple stop codons (e.g., TGA TGA) to increase the efficiency of translation termination.

The MAGE antigens can be administered in vectors described herein, and combined with checkpoint inhibitors in various vaccination schedules, including that in the Example, below.

c. Vector

The vaccine can comprise one or more vectors that include a nucleic acid encoding the antigen and the PD1 antibody or PDL1 antibody. The one or more vectors can be capable of expressing the antigen and the PD1 antibody or PDL1 antibody. The vector can have a nucleic acid sequence containing an origin of replication. The vector can be a plasmid, bacteriophage, bacterial artificial chromosome or yeast artificial chromosome. The vector can be either a self-replication extra chromosomal vector, or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, or the adjuvant-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen, or the adjuvant and enabling a cell to translate the sequence to an antigen that is recognized by the immune system, or the adjuvant.

Also provided herein is a linear nucleic acid vaccine, or linear expression cassette ("LEC"), that is capable of being efficiently delivered to a subject via electroporation and expressing one or more desired antigens, or one or more desired adjuvants. The LEC may be any linear DNA devoid of any phosphate backbone. The DNA may encode one or more antigens, or one or more adjuvants. The LEC may contain a promoter, an intron, a stop codon, and/or a polyadenylation signal. The expression of the antigen, or the adjuvant may be controlled by the promoter. The LEC may not contain any antibiotic resistance genes and/or a phosphate backbone. The LEC may not contain other nucleic acid sequences unrelated to the desired antigen gene expression, or the desired adjuvant expression.

The LEC may be derived from any plasmid capable of being linearized. The plasmid may be capable of expressing the antigen, or the PD1 antibody or PDL1 antibody. The plasmid may be capable of expressing the PD1 antibody or PDL1 antibody. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen, or encoding the adjuvant, and enabling a cell to translate the sequence to an antigen that is recognized by the immune system, or the adjuvant.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence, or the adjuvant sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be operably linked to the nucleic acid sequence encoding the adjuvant and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

d. Excipients and other Components of the Vaccine

The vaccine may further comprise a pharmaceutically acceptable excipient. The pharmaceutically acceptable excipient can be functional molecules such as vehicles, adjuvants other than the PD1 antibody or PDL1 antibody, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to the PD1 antibody or PDL1 antibody. The additional adjuvant can be other genes that are expressed in an alternative plasmid or are delivered as proteins in combination with the plasmid above in the vaccine. The adjuvant may be selected from the group consisting of: α-interferon(IFN-α), β-interferon (IFN-β), β-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants in addition to the PD1 antibody or PDL1 antibody include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Serial No. 021,579 filed Apr. 1, 1994, which is fully incorporated by reference. The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

3. Method of Vaccination

The present invention is also directed to a method of increasing an immune response in a subject. Increasing the immune response can be used to treat and/or prevent disease in the subject. The method can include administering the herein disclosed vaccine to the subject. The subject administered the vaccine can have an increased or boosted immune response as compared to a subject administered the antigen alone. In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

a. Administration

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccine can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Plymouth Meeting, Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

The present invention has multiple aspects, illustrated by the following non-limiting examples.

EXAMPLES

Example 1

Mice were immunized two times at two week intervals as three separate groups: vector pVAX only, DNA vaccine (HPV) only, and DNA vaccine (HPV) combined with mAb PDL1. For the combination, a mAb PD1 L was delivered beginning on day 10 post-first immuniziation, and thereafter every three days until mice were sacrificed 8 days after last immunization. The data, as shown in the bar graph in FIG. 1, shows a 30% increase in T cell responses induced by co-therapy with anti PDL1 antibody.

The PDL1 mAb can be generated or can be obtained commercially, e.g., CD274 (B7-H1, PD-L1) Rat Anti-Mouse mAb (clone 10F.9G2), PE-Cy®7 conjugate (Life Technologies).

Example 2 mAb

The PDL1, PD1, TIM-3 and LAG-3 mAb can be generated or can be obtained commercially, e.g., CD274 (B7-H1, PD-L1) Rat Anti-Mouse mAb (clone 10F.9G2), PE-Cy®7 conjugate (Life Technologies or Bio X cell), rat anti-mouse PD-1 (clone RMP1-14 or J43), rat anti-mouse TIM-3 (Clone RMT3-23; Bio X Cell), rat anti-mouse LAG-3 (Clone C9B7W; BIO X Cell), respectively.

Mouse Immunization

C57BL/6 mice (n=4) were immunized thrice, with a two-week interval between immunizations, with 25 µg hTERT construct with or without the delivery of either PD1, TIM3 and LAG3 mAb's.

Immunization Groups

Group II-hTERT
Group III-hTERT+PD1
Group IV-hTERT+TIM3
Group V-hTERT+LAG3

Each one of the mAb was delivered 3 days post-second immunization with hTERT.

Figure 2:
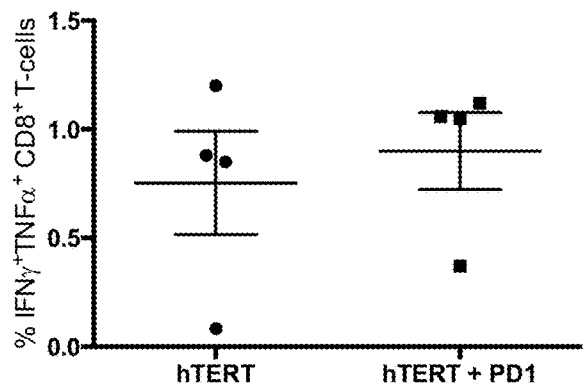
FIG. 2. Provides plot graphs that depict the total hTERT-specific CD8+ T cells expressing total IFNγ for mice treated with PD1. The left plot graph show the percentages of hTERT-specific CD3+CD8+ T cells displaying double release of the cytokines IFNγ and TNFα. Experiments were performed independently at least twice and data represent the mean±SEM of four mice per group.
Figure 2:
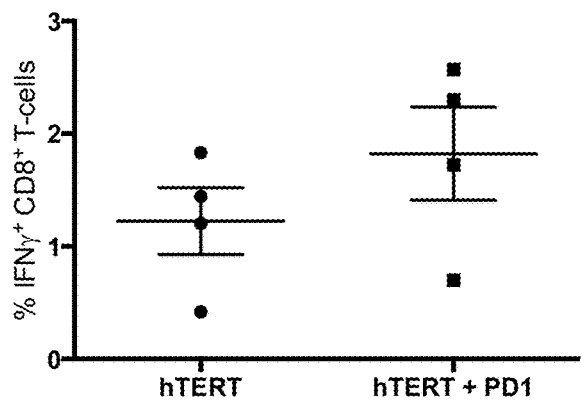
Figure 3:
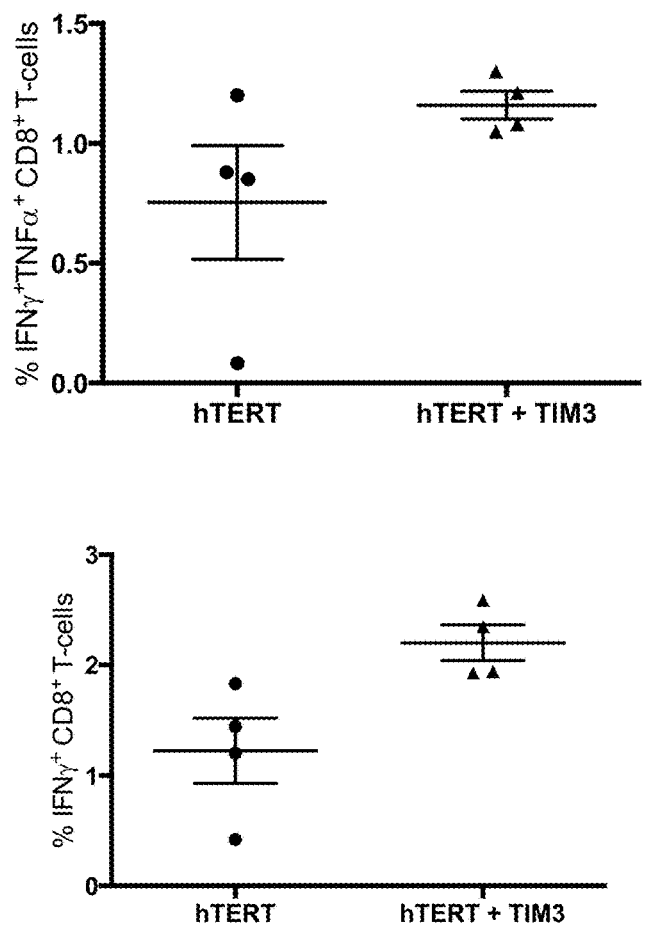
FIG. 3. Provides plot graphs that depict the total hTERT-specific CD8+ T cells expressing total IFNγ for mice treated with TIM3. The left plot graph show the percentages of hTERT-specific CD3+CD8+ T cells displaying double release of the cytokines IFNγ and TNFα. Experiments were performed independently at least twice and data represent the mean±SEM of four mice per group.
Figure 4:
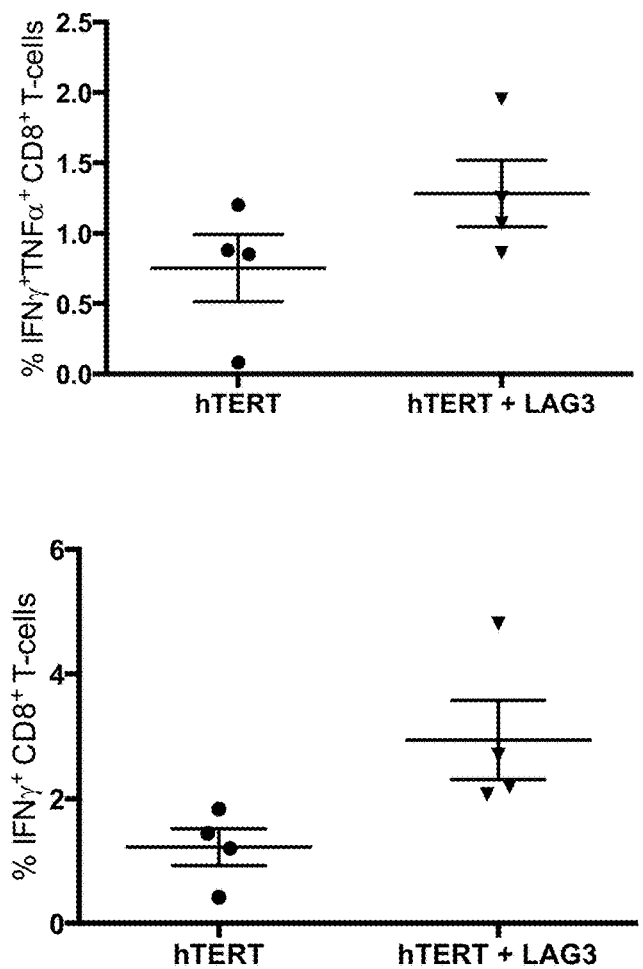
FIG. 4. Provides plot graphs that depict the total hTERT-specific CD8+ T cells expressing total IFNγ for mice treated with LAG3. The left plot graph show the percentages of hTERT-specific CD3+CD8+ T cells displaying double release of the cytokines IFNγ and TNFα. Experiments were performed independently at least twice and data represent the mean±SEM of four mice per group.

The data represented in the graphs in FIG. 2-4 show that the blockade of immune checkpoints after boost increases immune responses for anti PD-1, anti-TIM3, and anti-LAG3 antibodies. Induction of enhanced IFNγ production of hTERT-specific CD8+ T cells following DNA immunization with immune checkpoint inhibitors: Cytokine-recall responses to hTERT antigen were measured one week after last immunization by ICS and flow cytometry. The right plot graphs depict the total hTERT-specific CD8+ T cells expressing total IFNγ for mice treated with PD1 (FIG. 2), TIM3 (FIG. 3), and LAG3 (FIG. 4). The left plot graphs show the percentages of hTERT-specific CD3+CD8+ T cells displaying double release of the cytokines IFNγ and TNFα (PD1 in FIG. 2, TIM3 in FIG. 3, and LAG3 in FIG. 4. Experiments were performed independently at least twice and data represent the mean±SEM of four mice per group.

The results show surprisingly that the anti-TIM3 and anti-LAG3 antibodies produced significantly higher increase in immune response in the subjects.

Example 3

Timing of Checkpoint Inhibitor Delivery relative to Vaccination

Delivery of checkpoint inhibitors after prime immunization.

(A) Early Delivery:

C57BL/6 mice (n=3-4) were immunized twice, with a two-week interval between immunizations, with 25 µg hTERT construct with or without the delivery of either PD1, TIM3 and LAG3 mAb's. The initial mAb delivery of checkpoint inhibitors was at day 10 (D10), then D13, D16, and D19.

(B) Late Delivery

C57BL/6 mice (n=4) were immunized three times at three week intervals with 25 μg hTERT construct with or without the delivery of either PD1, TIM3, and LAG3 mAb's. The initial mAb delivery was at 3 days post-second immunization, and administered thereafter every three days until sacrificed.

Figure 5:
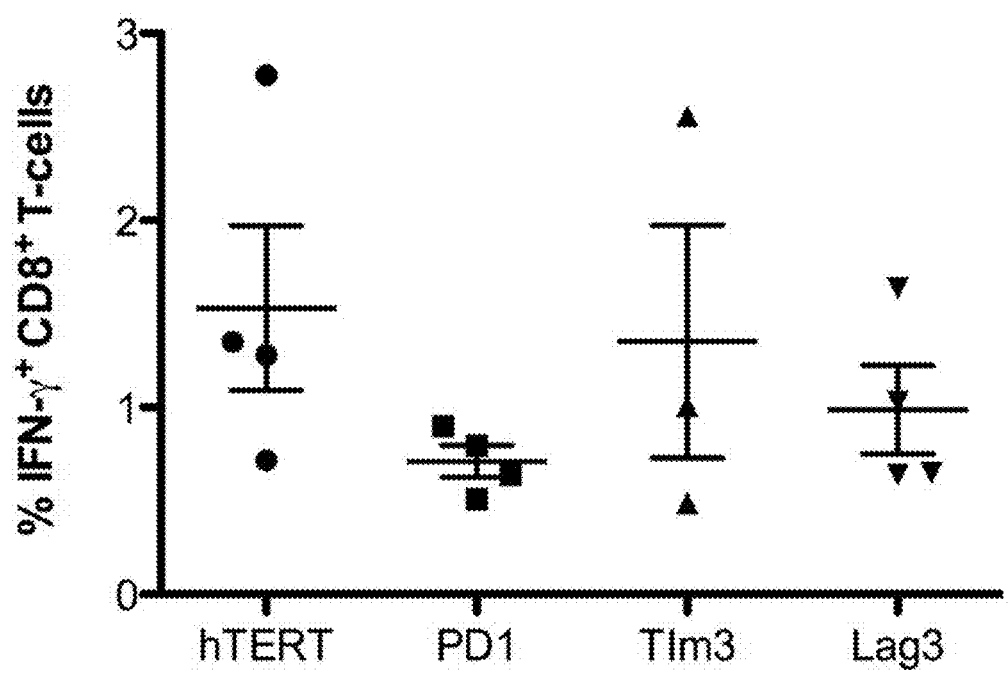
FIG. 5. Provides flow cytometry results for early delivery of mAb checkpoints. (A) shows plot graphs that depict the hTERT-specific CD8 T cells expressing total IFNγ for mice treated with or without PD1, TIM3 and LAG3 soon after priming immunization. (B) shows plot graphs that depict the hTERT-specific CD8 T cells expressing total IFNγ for mice treated with or without PD1, TIM3 and LAG3 soon after boost immunization.
Figure 6:
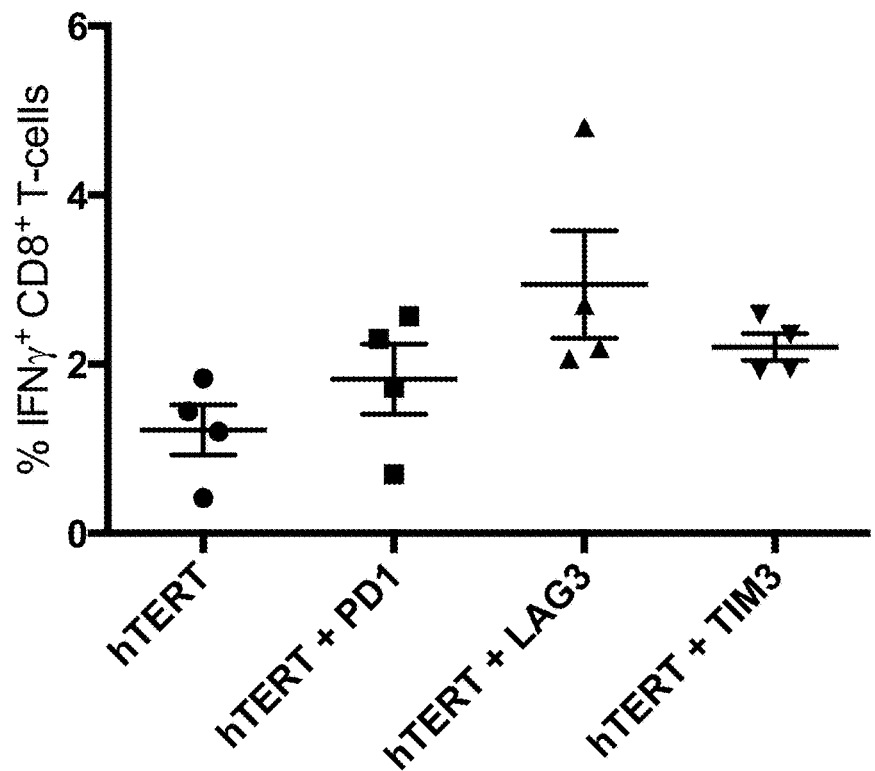
FIG. 6. Provides flow cytometry results for late delivery of mAb checkpoints. (A) shows plot graphs that depict the hTERT-specific CD8 T cells expressing total IFNγ for mice treated with or without PD1, TIM3 and LAG3 soon after priming immunization. (B) shows plot graphs that depict the hTERT-specific CD8 T cells expressing total IFNγ for mice treated with or without PD1, TIM3 and LAG3 soon after boost immunization.

Delivery of blockade immune checkpoint inhibitors is time sensitive. IFNγ-specific recall responses to hTERT antigen were measured one week after final immunization by flow cytometry during early delivery of mAb versus later delivery of mAb checkpoints. The plot graphs in FIG. 5 represents results for depicts the hTERT-specific CD8 T cells expressing total IFNγ for mice treated with or without PD1, TIM3 and LAG3 soon after priming immunization. The plot graphs in FIG. 6 depicts the hTERT-specific CD8 T cells expressing total IFNγ for mice treated with or without PD1, TIM3 and LAG3 soon after boost immunization. Thus, the data shows that late delivery yields surprising results in driving antigen specific T cell expansion by checkpoint inhibitors when compared with early delivery, which shows slower antigen specific immunity.

The invention claimed is:

1. A composition for generating hTERT-specific CD3+ CD8+ T cells displaying double release of the cytokines IFNγ and TNFα in a subject in need thereof, comprising:
   a) a monoclonal TIM-3 antibody or a monoclonal LAG-3 antibody, and
   b) a nucleic acid molecule comprising a nucleotide sequence encoding a synthetic hTERT antigen.

2. The composition of claim 1 wherein the synthetic antigen is an isolated DNA that encodes for the antigen.

3. The composition of claim 1, further comprising a pharmaceutically acceptable excipient.

* * * * *